United States Patent [19]

Kadin

[11] 4,175,193

[45] Nov. 20, 1979

[54] 2-AMINO-3-CYANO-4-HYDROXYQUINO-LINES

[75] Inventor: Saul B. Kadin, New London, Conn.

[73] Assignee: Pfizer Inc., New York, N.Y.

[21] Appl. No.: 890,738

[22] Filed: Mar. 27, 1978

Related U.S. Application Data

[63] Continuation-in-part of Ser. No. 759,295, Jan. 14, 1977, abandoned.

[51] Int. Cl.² .................. C07D 215/56; C07D 221/04
[52] U.S. Cl. ............................... 546/153; 260/465 E; 260/340.3; 260/340.5 R; 546/90; 546/110; 544/252
[58] Field of Search .................. 546/153, 110, 90

[56] References Cited

U.S. PATENT DOCUMENTS 3,647,802   3/1972   Carney ............................ 546/159

OTHER PUBLICATIONS

Coppola, et al., "J. Org. Chem.," vol. 41, 1976, pp. 825–831.

*Primary Examiner*—Alton D. Rollins
*Assistant Examiner*—James H. Turnipseed
*Attorney, Agent, or Firm*—Francis X. Murphy; Charles J. Knuth; Albert E. Frost

[57] ABSTRACT

The reaction of isatoic anhydrides with malononitrile in a reaction-inert solvent in the presence of a base to produce 2-amino-3-cyano-4-hydroxyquinolines and 2-amino-α,α-dicyanoacetophenones which are then hydrolyzed and decarboxylated under acid or base conditions to produce 2-amino-4-hydroxyquinolines, useful as intermediates for preparation of 1-oxo-1H-6-alkoxypyrimido[1,2-a]quinoline-2-carboxylic acids and esters of value as antiallergy agents.

6 Claims, No Drawings

2-AMINO-3-CYANO-4-HYDROXYQUINOLINES

CROSS REFERENCE TO RELATED APPLICATION

This application is a continuation-in-part of U.S. application Ser. No. 759,295, filed Jan. 14, 1977 and now abandoned.

BACKGROUND OF THE INVENTION

1. Field of the Invention

This invention relates to a process for production of 2-amino-4-hydroxyquinolines and to intermediates therefor. More particularly, it relates to the reaction of an isatoic anhydride with malononitrile in the presence of a base to produce as intermediate a 2-amino-α,α-dicyanoacetophenone and a 2-amino-3-cyano-4-hydroxyquinoline, followed by hydrolysis and decarboxylation of said intermediates under acid or base conditions.

2. Description of the Prior Art

The synthesis of 2-amino-4-hydroxyquinolines via the fusion of ethyl cyanoacetate with anilinium benzenesulfonate or p-toluenesulfonate is described by Hardman et al., *J. Chem. Soc.*, 3878 (1954). Gabriel, *Ber.*, 51, 1500 (1918) reports preparation of 2-amino-4-hydroxyquinoline by reduction of ethyl α-cyano-α-(o-nitrobenzoyl)acetate and by hydrolysis of α-cyano-α-(o-phthalimidobenzoyl)acetate. These methods, however, are characterized by relatively low yields, poor availability of necessary reactants and, in the case of the fusion procedure described above, limitation as to the amount of product which can be made in a single preparation.

For convenience, isatoic anhydride, the trivial but widely used and recognized name for 2H-3,1-benzoxazine-2,4(1H)-dione, is used throughout this document.

The reaction of N-alkyl isatoic anhydrides with malonic acid esters to produce N-alkylquinolinediones is reported by Coppola, et al, *J. Org. Chem.*, 41, 825 (1976). The replacement of malonic esters by compounds having an active methylene group and an electrophilic group capable of reacting with the liberated anilino nitrogen, for example, carbanions of the appropriate nitroacetate, phosphonoacetate, phosphonoacetonitrile or β-ketosulfone, permits introduction of nitrogen, phosphorous or sulfur substituents in the 3-position of the quinoline system.

Coppola, et al, (loc. cit.), also describe the reaction of N-(3-chloropropyl)isatoic anhydride and of N-(2-propynyl)isatoic anhydride with the sodium salt of malononitrile to produce 2,3,4,6-tetrahydro-6-oxo-1H-pyrimido[1,2-a]quinoline-5-carbonitrile and 1,2,3,5-tetrahydro-2-methylene-5-oxoimidazo[1,2-a]quinoline-4-carbonitrile, respectively.

SUMMARY OF THE INVENTION

It has now been found that 2-amino-4-hydroxyquinolines can be conveniently prepared by a process which comprises the steps of (a) reacting an isatoic anhydride with malononitrile in a reaction-inert solvent under basic conditions and (b) then treating the reaction product of step (a) thus produced with acid or base.

The process is of general applicability to the synthesis of 2-amino-4-hydroxyquinolines. Particular interest, however, resides in the 2-amino-4-hydroxyquinolines having the formula

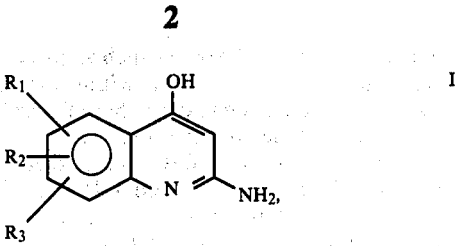

and acid addition salts thereof, wherein each of $R_1$, $R_2$ and $R_3$ is selected from the group consisting of hydrogen, alkyl having from 1 to 5 carbon atoms, alkoxy having from 1 to 5 carbon atoms, fluoro, chloro, bromo, methylthio and methylsulfinyl; with the proviso that no more than two of $R_1$, $R_2$ and $R_3$ are bulky groups; i.e., branched chain alkyl or branched chain alkoxy, and when two of said $R_1$, $R_2$ and $R_3$ are bulky groups they are located on non-adjacent positions;

$R_2$ and $R_3$ when taken together are selected from the group consisting of 1,3-butadienyl and alkylenedioxy of 1 to 2 carbon atoms;

because of their use as intermediates for production of 1-oxo-1H-6-alkoxypyrimido[1,2-a]quinoline-2-carboxylic acids and esters which are of value as antiallergy agents. These latter compounds, their preparation and use are described in Belgian Pat. No. 827,407, granted Oct. 1, 1975.

DETAILED DESCRIPTION OF THE INVENTION

Step (a) of the process of this invention, the reaction of an isatoic anhydride with malononitrile, is conducted in a reaction-inert solvent in the presence of a base.

Suitable solvents for this step are the following and mixtures thereof: N,N-dimethylformamide, N,N-dimethylacetamide, dimethylsulfoxide, 2,4-dimethyltetrahydrothiophene 1,1-dioxide, hexamethylphosphoramide, cyclic and acyclic ethers, alkanols especially those having up to ten carbon atoms, crown ethers (macrocyclic polyethers) such as those described by Pedersen in *J. Am. Chem. Soc.*, 89, 7017 (1967) and by Pedersen et al in *Angew. Chem. Internat. Edit.* 11, 16 (1972), and aromatic hydrocarbons such as benzene, xylene and toluene.

As illustrated herein, not all the reactants need be soluble in the particular solvent used. It is sufficient if either the isatoic anhydride reactant or the malononitrile be soluble in the solvent used, and that the reactants and products not enter into reaction with the solvent, except as noted below, under the reaction conditions used. The exception refers to possible reaction of the base with the solvent.

Bases suitable for the reaction of step (a) comprise a wide variety of bases of organic and inorganic nature which can be used. Representative organic bases are trialkylamines, especially those having from three to twelve carbon atoms; N-methylmorpholine and N,N-dimethylaniline. Representative inorganic bases are alkali metal amides, alkoxides, hydrides and hydroxides, especially those of sodium and potassium; triphenylmethyl sodium; and metallic sodium and potassium.

As the man skilled in the art will recognize, some of the useful bases enumerated above, particularly those of inorganic nature, will react with certain solvents. Metallic sodium or potassium, for example, will react with alkanols; and alkali metal hydroxides will react with crown ethers. Thus, depending upon the extent of its reaction with the solvent, the base added to the reaction may or may not be the base which actually expedites the reaction. However, included within the bases suitable for the reaction of step (a) are those formed by reaction of the added base with the solvent.

The reaction of step (a) is conducted at a temperature of from about 20° C. to about 150° C. The favored temperature is from about 50° C. to about 100° C. and the preferred range from about 50° C. to about 60° C.

The products of the reaction of step (a) are 2-amino-α,α-dicyanoacetophenones (formula III) and 2-amino-3-cyano-4-hydroxyquinolines (formula IV). It appears that formula III compounds are produced first and, under the conditions of the reaction, undergo partial cyclization to formula IV compounds, particularly if the reaction mixture is heated above 80° C. or is heated at 50°–60° C. for prolonged periods of time.

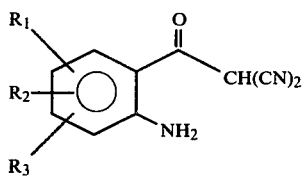

III

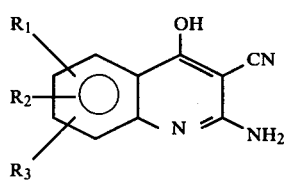

IV

The formation of a mixture of compounds of formulae III and IV in step (a) is immaterial to the overall process of this invention since, under the conditions of step (b), they are each converted to 4-hydroxyquinolines (formula I). Separation of the compounds is not necessary. For reasons of convenience and economy, it is preferred to use the reaction product of step (a) without purification in step (b). They are recovered by acidifying the reaction mixture, for example by pouring the reaction mixture into cold dilute hydrochloric acid. The resulting precipitate, a mixture of the above-named products, is then treated with acid or base, step (b), to produce the desired 2-amino-4-hydroxyquinolines.

In step (b), the reaction product of step (a) is treated with a strong acid or a strong base at a temperature ranging from about 80° C. to about 150° C. Higher temperatures appear to offer no advantage and may even reduce the yield of the desired product as a result of degradation reactions. At lower temperatures the reaction is so slow as to be of no practical use.

The choice of acid or base conditions to convert the reaction product of step (a) to the desired 2-amino-4-hydroxyquinoline is dependent upon the value of the $R_1$, $R_2$ and $R_3$ substituents. When $R_1$, $R_2$ or $R_3$ is a group which would undergo reaction with acid, e.g., an ether group, and retention of said group in its original form is desired, then a base is used in step (b) to achieve the aforesaid conversion. If hydrolysis of the ether group is desired, then, of course, an acid, e.g. HBr, can be used to accomplish the conversion of the step (a) reaction product to a 2-amino-4-hydroxyquinoline and hydrolysis of the ether group in a single step.

The isolated reaction product of step (a) is suspended in a strong acid or strong base and the resulting mixture heated to a temperature of from about 80° C. to about 125° C. Suitable strong acids are hydrobromic acid, hydrobromic acid-acetic acid, sulfuric acid and hydrochloric acid. When using hydrochloric acid, the reaction is carried out under pressure as, for example, in a glass bomb. The favored acid is hydrobromic acid, especially 48% hydrobromic acid, since it affords good yields of the desired 2-amino-4-hydroxyquinolines in a readily isolable form, i.e., as the hydrobromide salts.

The products resulting from acid treatment of step (a) reaction products are isolated in the form of their acid addition salts corresponding to the acid used by chilling the reaction mixture, or by evaporation. They are converted to their base form by neutralization of an aqueous solution (or suspension) of the acid with base. The 2-amino-4-hydroxyquinoline products generally precipitate and are recovered by filtration. If precipitation of the 2-amino-4-hydroxyquinoline product does not occur, it is recovered by evaporation or by addition of a water-miscible organic solvent to precipitate it from the solution.

As noted above, conversion of the reaction product of step (a) to a 2-amino-4-hydroxyquinoline can also be accomplished by treatment with a strong base. Suitable strong bases are the alkali metal hydroxides, especially aqueous solutions of sodium or potassium hydroxide of 6N or higher concentration, since they afford satisfactory yields of desired 2-amino-4-hydroxyquinolines. The products are recovered by neutralization of the alkaline reaction mixture to precipitate the free 2-amino-4-hydroxyquinoline.

Many of the required isatoic anhydride reactants are available commercially. Those which are not are conveniently synthesized from the appropriate anthranilic acid and phosgene according to the procedure reported by Wagner et al., Org. Syn., Coll. Vol. III, 488 (1955). The requisite anthranilic acids, if not known compounds, are readily obtainable from appropriately substituted phthalic anhydrides by methods known to those skilled in the art. A typical procedure would, for example begin with the appropriate phthalic anhydride which is converted to phthalimide by reaction with ammonia followed by reaction of the thus-produced phthalimide with sodium hypochlorite in alkaline solution at a temperature of 75°–85° C. (see Fieser and Fieser, "Organic Chemistry," D. C. Heath and Company, Boston, Mass., 1944, p. 671).

The 2-amino-4-hydroxyquinolines are valuable intermediates for production of 1-oxo-1H-6-alkoxypyrimido[1,2a]quinoline-2-carboxylic acids and its esters which are useful as antiallergy agents and have the formula

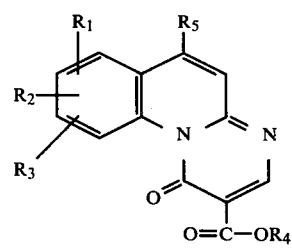

wherein $R_1$, $R_2$ and $R_3$ are as defined above; $R_4$ is hydrogen or alkyl; and $R_5$ is alkoxy having from 1 to 5 carbon atoms.

Compounds of formula II are prepared from 2-amino-4-hydroxyquinolines by the reaction sequence comprising conversion of the appropriate 2-amino-4-hydroxyquinoline to a 2-amino-4-alkoxyquinoline by reaction with a lower alkyl ester of an arylsulfonic acid or by reaction, as their sodium salts, with a lower alkyl halide. The thus-produced 2-amino-4-alkoxyquinolines are then condensed with a dialkyl ethoxymethylenemalonate in a reaction-inert solvent at from 80° C. to 125° C., to give a dialkyl 4-alkoxy-2-quinolylaminomethylenemalonate which is then cyclized by heating from 175° C. to 250° C. in a reaction-inert solvent such as a mixture of diphenyl ether and diphenyl, especially that which contains 26.5% diphenyl and 73.5% diphenyl ether and is sold under the trademark Dowtherm A (Dow Chemical Co., Midland, Mich.).

The thus-produced alkyl 1-oxo-1H-6-alkoxypyrimido[1,2-a]quinoline-2-carboxylates are then hydrolyzed to the corresponding acids, for example, by heating an aqueous mixture of the appropriate ester with hydrochloric acid at from about 50° C. to 100° C. until hydrolysis is complete. The acids are recovered by filtration if they precipitate upon cooling the reaction mixture, or by evaporation of the reaction mixture.

They can be administered either as individual therapeutic agents or as mixtures of therapeutic agents; for example, with theophylline or sympathomimetic amines, with or without a pharmaceutical carrier selected on the basis of the chosen route of administration and standard pharmaceutical practice. For example, they can be combined with various pharmaceutically-acceptable inert carriers in the form of tablets, capsules, aerosol sprays, aqueous suspensions or solutions, injectable solutions, elixirs, syrups and the like.

For the purpose of parenteral administration and inhalation, solutions or suspensions of these compounds in sesame or peanut oil or in aqueous propylene glycol solutions can be employed. These particular solutions are especially suited for intramuscular and subcutaneous injection purposes should such method of administration be desired. The aqueous solutions are also useful for intravenous injection purposes provided that their pH is properly adjusted beforehand.

The compounds can be administered to asthmatic subjects suffering from bronchoconstriction by means of inhalators or other devices which permit the active compounds to come into direct contact with the constricted areas of the tissues of the subject.

The dosage regimen of said compounds will, of course, vary with age, weight and response of the particular patient as well as with the nature and extent of the symptoms, the pharmacodynamic characteristics of the particular agent to be administered and the route of administration chosen.

An effective daily oral dosage of said compounds in humans of from about 10 to about 1500 mg. per day, with a preferred range of about 10 to about 600 mg. per day in single or divided doses, or at about 0.2 to about 2 mg./kg. of body weight will effectively alleviate bronchoconstriction in human subjects.

When administered intravenously or by inhalation, the effective daily dose is from about 0.5 to about 400 mg. per day, and preferably from about 0.25 to 200 mg. per day, or at about 0.005 to 4 mg./kg. of body weight in single or divided doses.

The antiallergy property of the 1-oxo-1H-6-alkoxypyrimido[1,2-a]quinoline-2-carboxylic acids and esters is evaluated by the passive cutaneous anaphylaxis (PCA) test (Ovary, *J. Immun.*, 81, 355, 1958). In the PCA test, normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

EXAMPLE 1

2-Amino-4-hydroxyquinoline

A solution of isatoic anhydride (49.8 g., 0.3 mole) in 300 ml. of N,N-dimethylformamide is added, during 30 minutes, to a warm (50°-60° C.) solution of malononitrile (21.8 g., 0.33 mole) and triethylamine (33.4 g., 0.33 mole) in 100 ml. of N,N-dimethylformamide. Brisk evolution of carbon dioxide is observed. The reaction mixture is maintained at 50°-60° C. for 30 minutes after addition of the anhydride is completed and is then poured into 2500 ml. of ice-cold 0.2 N hydrochloric acid. The precipitate which forms is isolated by filtration and dried. It is then suspended in 48% hydrobromic acid (1500 ml.) and the mixture refluxed for 20 hours. The resulting clear solution is chilled in an ice bath and the precipitate which forms collected by filtration. It is then dissolved in warm water and, after filtering to remove a small amount of insoluble material, the solution is made alkaline with ammonium hydroxide. The resulting precipitate is filtered, washed with water and isopropanol, and dried to give 41.2 g. (86%) of product; m.p. 298°-300° C., dec. An analytical sample is recrystallized from methanol-water, m.p. 300° C., dec.

Analysis: Calc'd for $C_9H_8N_2O$: C, 67.47; H, 5.03; N, 17.49%. Found: C, 67.23; H, 5.12; N, 17.50%.

MS: m/e=160 (m+).

Repetition of this reaction but replacing triethylamine with N-methylmorpholine, N,N-dimethylaniline, tri-n-butylamine, N-decyl dimethylamine, N-hexyl dimethylamine, sodamide, triphenylmethyl sodium, sodium hydride, potassium ethoxide, metallic sodium, or potassium hydroxide, affords the same product.

EXAMPLE 2

2-Amino-4-hydroxy-6-methylquinoline

A solution of 5-methyl isatoic anhydride (19.5 g., 0.11 mole) in 150 ml. of N,N-dimethylformamide is added, during 15 minutes, to a warm (55°-60° C.) solution of malononitrile (7.9 g., 0.12 mole) and triethylamine (12.1 g., 0.12 mole) in N,N-dimethylformamide (100 ml.). Carbon dioxide is evolved and the reaction mixture is stirred for 30 minutes after addition of the anhydride is complete without further heating. The resulting clear, dark solution is poured into ice-cold 0.2 N hydrochloric acid (1220 ml.). The solid which separates is isolated by filtration and dried (19.5 g.). A portion of said solid (9.5 g.) is then suspended in 48% hydrobromic acid (250 ml.)—acetic acid (50 ml.) and the mixture refluxed for 20 hours. The clear solution that results is chilled in an ice bath and the precipitate which forms is collected by filtration. It is dissolved in ethanol-water (200 ml. of 1:1) and, after filtering to remove a small amount of insoluble material, the filtrate made alkaline with ammonium hydroxide. Crushed ice is added and the solid which precipitates is filtered and dried: 6.2 g. (73%); m.p. 343° C. (dec.).

An analytical sample is prepared by recrystallization from methanol-water.

Analysis: Calc'd for $C_{10}H_{10}N_2O$: C, 68.94; H, 5.79; N, 16.08%. Found: C, 68.75; H, 5.84; N, 16.06%.

EXAMPLE 3

2-Amino-6-chloro-4-hydroxyquinoline

Following the procedure of Example 2, 5-chloroisatoic anhydride (19.8 g., 0.1 mole), malononitrile (7.3 g., 0.11 mole) and triethylamine (11.1 g., 0.11 mole) are reacted together in N,N-dimethylformamide (200 ml.) to give 20 g. of product. Five grams of said product are refluxed for 22 hours in 48% hydrobromic acid (175 ml.) to give 4.2 g. (86%) yield of title product; m.p. 356° C. (dec.).

Analysis: Calc'd for $C_9H_7ClN_2O$: C, 55.54; H, 3.63; N, 14.40%. Found: C, 55.17; H, 3.68; N, 14.26%.

Repetition of this procedure but using 12 N sulfuric acid in place of hydrobromic acid affords the same product.

EXAMPLE 4

2-Amino-6-methoxy-4-hydroxyquinoline

To a solution of malononitrile (6.0 g., 0.91 mole) and triethylamine (9.2 g., 0.091 mole) in N,N-dimethylformamide (50 ml.) at 55°-60° C. is added rapidly, and with stirring, a solution of 5-methoxy isatoic anhydride in N,N-dimethylformamide (100 ml.). The reaction mixture is maintained at 55°-60° C. during addition. Carbon dioxide is evolved and the reaction mixture is stirred for a half-hour following completion of addition without application of further heating. The clear solution is poured into 0.2 N of cold hydrochloric acid (1015 ml.) and the resulting precipitate separated by filtration and dried; 16.5 g.; m.p. >370° C.

A portion of said product (1.08 g.) is added to 6 N potassium hydroxide solution (20 ml.) and the mixture heated to reflux for about 18 hours. The clear, dark solution formed is cooled and acidified with acetic acid. The dark brown solid which precipitates is filtered, taken up in ethanol-water (1:2, 30 ml.) and the solution made alkaline with ammonium hydroxide. The resulting solid is filtered and dried. Yield=710 mg (69%); m.p. 298°-300° C.

MS: m/e=190 (m+).

Analysis: Calc'd for $C_{10}H_{10}N_2O_2$: C, 63.14; H, 5.30; N, 14.73%. Found: C, 62.85; H, 5.23; N, 14.56%.

EXAMPLE 5

2-Amino-α,α-Dicyanoacetophenone

To a solution of malononitrile (7.3 g., 0.11 mole) in N,N-dimethylformamide (150 ml.) is added sodium hydride (4.7 g., 0.11 mole) Carbon dioxide is evolved and the mixture is stirred for ten minutes. Isatoic anhydride (16.3 g., 0.10 mole) is added to the reaction mixture which is then heated to 50°-60° C. for 30 minutes. The reaction mixture is then cooled and poured into cold water (1000 ml.). The aqueous mixture is filtered to remove a small amount of amorphous precipitate. The filtrate is made strongly acid with concentrated hydrochloric acid and the resulting precipitate separated by filtration, washed with water and dried (18.0 g.) M.P.=>300° C. Infrared analysis (Nujol) of the product showed complete absence of carbonyl absorption and a strong C≡N peak at 4.5μ. The product gives a positive ferric chloride test.

EXAMPLE 6

2-Amino-3-cyano-4-hydroxyquinoline

The product of Example 5 is recrystallized from N,N-dimethylformamide to give a colorless crystalline product; M.P.>360° C. Infrared analysis in Nujol shows carbonyl absorption at 6μ and C≡N absorption at 4.5μ. The product gives a negative chloride test.

Analysis: Calc'd for $C_{10}H_7N_3O$: C, 64.86; H, 3.81; N, 22.69%. Found: C, 64.69; H, 4.00; N, 22.55%.

EXAMPLE 7

2-Amino-4-hydroxyquinoline

The product of Example 5 is suspended in 48% hydrobromic acid (30 ml. per gram) and the mixture refluxed for 20 hours. The resulting clear solution is chilled in an ice bath and the precipitate which forms collected by filtration. It is dissolved in warm water, the solution filtered and the filtrate made alkaline with ammonium hydroxide. The precipitate which forms is filtered, washed with water and isopropanol, and air dried. The product is identical to that of Example 1.

Similarly, the product of Example 6 is converted to the title compound.

EXAMPLE 8

The procedures of Examples 1 and 4 are repeated but using the appropriate isatoic anhydride as reactant to give the following compounds. When any of $R_1$, $R_2$ or $R_3$ is alkoxy, the procedure of Example 4 is used.

| $R_1$ | $R_2$ | $R_3$ |
|---|---|---|
| 7-OCH$_3$ | H | H |
| 6-OCH$_3$ | 7-OCH$_3$ | H |
| 6-OC$_2$H$_5$ | H | H |
| 6-F | H | H |
| H | 7-F | H |
| H | 7-Cl | H |
| 6,7-CH=CH—CH=CH— | | H |
| 5-CH$_3$ | H | 8-OCH$_3$ |
| H | H | 8-OCH$_3$ |
| H | H | 8-Cl |
| 6-CH$_3$ | H | 8-CH$_3$ |
| 6-i-C$_3$H$_7$ | H | H |
| 6,7-O—CH$_2$—O— | | H |
| H | | 7,8-O—CH$_2$—O— |
| 5-Br | H | H |
| H | H | 8-Br |
| H | 6-n-C$_4$H$_9$ | H |
| H | 6-sec-C$_4$H$_9$ | H |
| H | 6-t-C$_4$H$_9$ | H |
| 5-Cl | H | H |
| H | H | 8-C$_2$H$_5$ |
| H | 6-C$_2$H$_5$ | H |
| H | 6-OH | H |
| H | H | 7-OH |
| 5-OH | H | H |
| 5-OCH$_3$ | H | 8-OCH$_3$ |
| 7-OC$_2$H$_5$ | H | 8-OH |
| 5-CH$_3$ | H | 7-CH$_3$ |
| 5,6-O—CH$_2$—O— | | H |
| 6-O-i-C$_3$H$_7$ | 7-O-i-C$_3$H$_7$ | H |
| 6-OH | H | 8-OH |
| 6-F | 7-F | H |

-continued

[Structure: quinoline with R1, R2, R3 substituents, 4-OH, 2-NH2]

| R1 | R2 | R3 |
|---|---|---|
| 6-OC$_2$H$_5$ | 7-OC$_2$H$_5$ | H |
| 6-t-C$_4$H$_9$ | 8-t-C$_4$H$_9$ | H |
| H | 7-Br | 8-Br |
| H | 7-Cl | 8-OH |
| 6,7-O—CH$_2$—CH$_2$—O— | | H |
| 5-OCH$_3$ | H | 7-OCH$_3$ |
| 5-OC$_2$H$_5$ | H | 8-OC$_2$H$_5$ |
| H | 6-i-C$_3$H$_7$ | 8-i-C$_3$H$_7$ |
| H | 6-SCH$_3$ | H |
| H | 6-SOCH$_3$ | H |
| H | H | 7-SCH$_3$ |
| 6-O-n-C$_4$H$_9$ | 7-O-n-C$_4$H$_9$ | H |
| H | 6-O-n-C$_3$H$_7$ | 7-Br |
| 5-Cl | 6-O-n-C$_3$H$_7$ | 8-Cl |
| 5-Br | 6-SCH$_3$ | 7-Br |
| H | H | 7-n-C$_4$H$_9$ |
| 5-Cl | 6-O-n-C$_3$H$_7$ | 7-Cl |
| H | 6-SCH$_3$ | 7-Cl |
| H | 6-SOCH$_3$ | 7-Cl |
| H | 6-Cl | 7-SCH$_3$ |
| H | 6-Cl | 7-SOCH$_3$ |
| H | 6-SCH$_3$ | 7-SOCH$_3$ |
| H | 6-SCH$_3$ | 7-SCH$_3$ |
| H | 6-SOCH$_3$ | 7-SOCH$_3$ |
| 6-OCH$_3$ | 7-OCH$_3$ | 8-OCH$_3$ |
| 5-OCH$_3$ | 6-OCH$_3$ | 7-OCH$_3$ |
| 5-Cl | 7-Cl | H |
| 6-Cl | 7-Cl | H |
| 5-Cl | 6-Br | H |
| H | 7,8-CH=CH—CH=CH— | |
| 5-Br | 7-Br | 8-OH |
| 5-Cl | 7-Cl | 8-OH |
| 5-OH | 6-CH$_3$ | 8-OH |
| 6-OCH$_3$ | 7-OH | 8-OCH$_3$ |
| 6-CH$_3$ | 7-CH$_3$ | 8-OH |
| 6-CH$_3$ | 7-OH | 8-CH$_3$ |
| H | H | 8-O-n-C$_5$H$_{11}$ |
| 6-F | 7-F | 8-F |
| H | 5-SCH$_3$ | 8-CH$_3$ |
| 7-t-C$_5$H$_{11}$ | H | H |
| 7-CH$_3$ | 8-CH$_3$ | 5-i-C$_4$H$_9$ |
| 5-OH | 7-OCH$_3$ | 8-CH$_3$ |

EXAMPLE 9

2-Amino-4-hydroxyquinoline

The procedure of Example 1 is repeated on one-tenth the scale described therein and using concentrated hydrochloric acid in a sealed tube in place of 48% hydrobromic acid. The hydrochloric acid treatment is conducted at 125° C. The product is identical to that of Example 1.

EXAMPLE 10

The procedure of Example 5 is repeated but using the appropriate isatoic anhydride to provide the following compounds:

[Structure: benzene with R1, R2, R3, C(=O)—CH(CN)$_2$, NH$_2$]

| R1 | R2 | R3 |
|---|---|---|
| 5-CH$_3$ | H | H |
| 5-Cl | H | H |
| 5-OCH$_3$ | H | H |
| 6-OCH$_3$ | 7-OCH$_3$ | H |
| H | 7-F | H |
| H | H | 8-Br |
| H | 6-t-C$_4$H$_9$ | H |
| 3-Cl | H | H |
| 3-Br | 5-Br | H |
| 3-OH | 4-Cl | H |
| 4-CH$_3$ | 5-CH$_3$ | H |
| 4-OC$_2$H$_5$ | 5-OC$_2$H$_5$ | H |
| 5,6-O—CH$_2$—CH$_2$—O— | | H |
| 6,7-O—CH$_2$—O— | | H |
| 6,7-CH=CH—CH=CH— | | H |
| 4-OCH$_3$ | 5-OCH$_3$ | 6-OCH$_3$ |
| H | 6-SCH$_3$ | 7-Cl |
| H | 6-SOCH$_3$ | 7-Cl |
| H | 6-SOCH$_3$ | 7-SOCH$_3$ |
| H | 6-Cl | 7-SCH$_3$ |
| 5-Cl | 7-Cl | H |
| 6-O-n-C$_4$H$_9$ | 7-O-n-C$_4$H$_9$ | H |
| H | 6-i-C$_3$H$_7$ | 8-i-C$_3$H$_7$ |
| 4-t-C$_5$H$_{11}$ | H | H |
| 3-F | 4-F | 6-F |
| 3-CH$_3$ | 4-OCH$_3$ | 6-OH |
| 3-CH$_3$ | 4-OH | 5-CH$_3$ |
| 3-OH | 4-CH$_3$ | 6-CH$_3$ |
| 3-OH | 4-Cl | 6-Cl |
| 3-CH$_3$ | 6-SCH$_3$ | H |
| 3-O-n-C$_5$H$_{11}$ | H | H |
| 3-CH$_3$ | 4-CH$_3$ | 6-i-C$_4$H$_9$ |

EXAMPLE 11

Repetition of the procedure of Example 6 but using the appropriate isatoic anhydride affords the following compounds:

[Structure: quinoline with R1, R2, R3, 4-OH, 3-CN, 2-NH$_2$]

| R1 | R2 | R3 |
|---|---|---|
| 5-CH$_3$ | H | H |
| 6-F | H | H |
| H | 7-F | H |
| 6-CH$_3$ | 7-CH$_3$ | H |
| H | 6-n-C$_4$H$_9$ | H |
| 5-OH | H | H |
| 5-OCH$_3$ | H | 8-OCH$_3$ |
| 5-OCH$_3$ | 6-OCH$_3$ | 7-OCH$_3$ |
| 6,7—CH=CH—CH=CH— | | H |
| H | | 7,8-O—CH$_2$—O— |
| 5-Cl | 6-O-n-C$_3$H$_7$ | 8-Cl |
| 5-Br | 6-SCH$_3$ | 7-Br |
| H | 6-SCH$_3$ | 7-SCH$_3$ |
| H | 6-SOCH$_3$ | 7-SOCH$_3$ |
| 7-OC$_2$H$_5$ | H | 8-OH |
| 5-OH | 7-OCH$_3$ | 8-CH$_3$ |
| 5-CH$_3$ | 7-CH$_3$ | 8-OH |
| 7-t-C$_5$H$_{11}$ | H | H |
| 7-CH$_3$ | 8-CH$_3$ | 5-i-C$_4$H$_9$ |
| 6-F | 7-F | 8-F |

-continued

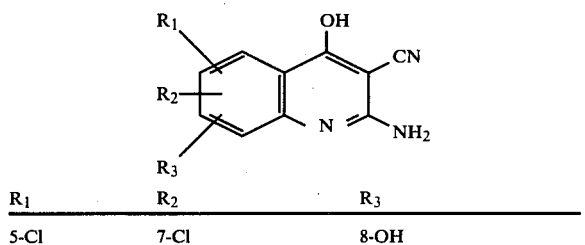

| R₁ | R₂ | R₃ |
|---|---|---|
| 5-Cl | 7-Cl | 8-OH |

EXAMPLE 12

The products of Examples 10 and 11 are hydrolyzed and decarboxylated according to the procedure of Example 7 to provide compounds having the formula shown below wherein R₁, R₂, and R₃ are as defined in Examples 10 and 11:

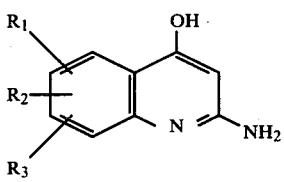

PREPARATION A

Ethers of 2-Amino-4-hydroxyquinoline via Esters of p-Toluenesulfonic Acid

A mixture of the appropriate 2-amino-4-hydroxyquinoline and the appropriate alkyl p-toluenesulfonate (10 to 20% molar excess) in xylene (from about 1-2 liters per mole of quinoline compound) is heated at reflux for 4-5 hours. It is then cooled, filtered and the filter cake washed with xylene. The solid is slurried in 3 N KOH for 15-20 minutes and then filtered. The filter cake is washed with water, dried and recrystallized from a suitable solvent.

via Alkylation with Alkyl Bromide

Equimolar amounts of the appropriate 2-amino-4-hydroxyquinoline and sodium hydride are reacted in warm N,N-dimethylformamide to produce the sodio derivative of the 2-amino-4-hydroxyquinoline. An equimolar amount of the alkyl bromide reactant is added and the reaction mixture heated for 20 minutes on a steam bath. It is then poured into water, the ether product separated by filtration or extracted with a suitable solvent such as benzene or chloroform. The extract is dried ($Na_2SO_4$) and evaporated. The products are crystallized from suitable solvents.

When any of R₁, R₂ or R₃ is hydroxy, sufficient quantities of sodium hydride and the appropriate alkylbromide are used to convert all hydroxy groups to ether groups.

PREPARATION B

Ethyl 1-Oxo-1H-6-methoxypyrimido[1,2-a]quinoline-2-carboxylate

A. A mixture of 2-amino-4-methoxyquinoline (34 g., 0.196 mole) and diethyl ethoxymethylenemalonate (46.8 g., 0.216 mole) is heated on a steam bath. A clear melt forms within about ten minutes and within about twenty minutes begins to resolidify. The mixture is heated a total of 45 minutes and is then cooled. The product, diethyl 4-methoxy-2-quinolylaminomethylenemalonate, is crystallized from ethanol (350 ml.) as a fluffy solid; m.p. 136.5°-137.5° C.

B. To Dowtherm A (350 ml.) at 100° C. is added the product from A (55 g. 0.16 mole) and the resulting clear yellow solution heated to 230°-233° C. for 1.75 hours. The reaction mixture is cooled, diluted with ethyl acetate (500 ml.) and then extracted with 1 N hydrochloric acid (3×120 ml.). The extracts are combined, made basic with 20% ammonium hydroxide and chilled to precipitate the product. It is filtered and recrystallized successively from ethanol, benzene-cyclohexane (1:1) and ethanol to give 15.5 g. of the ethyl ester as yellow crystals; m.p. 130°-130.5° C.

By means of the above preparations, the 2-amino-4-hydroxyquinolines described herein are converted to corresponding ethyl 1-oxo-1H-6-lower alkoxypyrimido[1,2-a]quinoline-2-carboxylates.

PREPARATION C

1-Oxo-1H-6-methoxypyrimido[1,2-a]quinoline-2-carboxylic Acid

A mixture of ethyl 1-oxo-1H-6-methoxypyrimido[1,2-a]quinoline-2-carboxylate (3.0 g.) and concentrated hydrochloric acid (60 ml.) is heated on a steam bath for a half hour. It is then cooled and filtered to give 0.87 g. of the title product. It is recrystallized from N,N-dimethylformamide m.p. 219° C. (dec.)

In like manner, the products of Preparation B are hydrolyzed to the corresponding acids.

What is claimed is:

1. A compound having the formula:

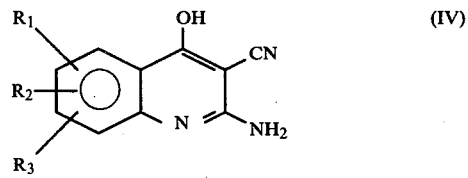

wherein each of R₁, R₂ and R₃ is selected from the group consisting of hydrogen, alkyl having from 1 to 4 carbon atoms, alkoxy having from 1 to 4 carbon atoms, chloro, bromo, fluoro, hydroxy, methylthio and methylsulfinyl, and R₂ and R₃ when taken together are selected from the group consisting of 1,3-butadienyl and alkylenedioxy having from 1 to 2 carbon atoms.

2. A compound according to claim 1 wherein R₁ is methyl and each of R₂ and R₃ is hydrogen.

3. A compound according to claim 1 wherein R₃ is hydrogen and each of R₁ and R₂ is alkoxy.

4. The compound according to claim 3 wherein R₁ is 6-methoxy and R₃ is 7-methoxy.

5. The compound according to claim 1 wherein each of R₁, R₂ and R₃ is hydrogen.

6. A compound according to claim 1 wherein each of R₁ and R₃ is hydrogen and R₂ is fluoro.

* * * * *